United States Patent [19]

Forstinger et al.

[11] Patent Number: 5,594,145

[45] Date of Patent: Jan. 14, 1997

[54] PROCESS FOR THE PREPARATION OF 2(3H)-BENZOTHIAZOLONES

[75] Inventors: Klaus Forstinger, Kelsterbach; Heinrich Volk, Bad Vilbel; Werner Wykypiel, Gründau, all of Germany

[73] Assignee: Hoechst AG, Germany

[21] Appl. No.: 232,748

[22] Filed: Apr. 25, 1994

[30] Foreign Application Priority Data

Apr. 28, 1993 [DE] Germany .......................... 43 13 930.2

[51] Int. Cl.⁶ .............................................. C07D 277/68
[52] U.S. Cl. ............................................ 548/173; 548/165
[58] Field of Search ...................................... 548/165, 173

[56] References Cited

U.S. PATENT DOCUMENTS 3,888,871  7/1985  Lowe ........................................ 548/173

FOREIGN PATENT DOCUMENTS 0245991  11/1987  European Pat. Off. .
2360202   7/1974  Germany .
966496    8/1964  United Kingdom .

OTHER PUBLICATIONS

European Search Report, Jul. 13, 1994, No. 94 106 198.8.
Elderfield, J. Org. Chem. 18 1092 (1953).
Erlenmeyer, Helv. Chim Acta, 27 1432 (1944).

*Primary Examiner*—Robert Gerstl
*Attorney, Agent, or Firm*—Connolly & Hutz

[57] ABSTRACT

The process for the preparation of 2(3H)-benzothiazolones which are optionally substituted on the benzene ring by reacting a 2-aminobenzothiazole which is optionally substituted on the benzene ring with a diazotization agent in the presence of aqueous hydrochloric acid, if appropriate with addition of a chloride, to give a diazonium chloride, reacting the diazonium chloride directly to give a 2-chlorobenzothiazole, which is optionally substituted on the benzene ring, and hydrolyzing the 2-chlorobenzothiazole, without intermediate isolation, at 120°–200° C. under reaction pressure.

24 Claims, No Drawings

PROCESS FOR THE PREPARATION OF 2(3H)-BENZOTHIAZOLONES

The invention relates to a process for the preparation of optionally substituted 2(3H)-benzothiazolones.

2(3H)-Benzothiazolones represent intermediate products for the preparation of agrochemicals such as, for example, 4-chloro-2,3-dihydro-2-oxo-benzothiazolyl-3-ylacetic acid (British Patent Specification 966,496).

A range of syntheses are known for the preparation of 2(3H)-benzothiazolones:

1) Cyclization of 2-aminothiophenols with phosgene, chlorocarbonates, ureas or carbonyl sulfide;
2) reductive carbonylation of substituted nitrobenzenes using sulfur, carbon monoxide and water in the presence of bases;
3) cyclization of thiocarbamates and subsequent ether cleavage of the 2-alkoxybenzothiazoles formed;
4) oxidation of 2-mercaptobenzothiazoles or benzothiazolyl alkyl thioethers to give 2-sulfonyl- or 2-alkylsulfonylbenzothiazoles, followed by hydrolysis;
5) reaction of o-nitrochlorobenzenes with thioglycolic acid, cyclocondensation of the o-nitrophenylthioacetic acid formed with acetic anhydride and deacylation;
6) reaction of 2-aminobenzothiazoles with alkali metal hydroxides or alkaline earth metal hydroxides in an anhydrous medium and cyclization of the o-mercaptophenylureas formed;
7) JP-021193 describes the preparation of 3-substituted 2(3H)-benzothiazolones by nitrosation of 3-substituted 2(3H)-iminobenzothiazoles andhydrolysis in xylene/hydrochloric acid.

The processes described under 1–6 have the disadvantage that they are based on mercapto compounds which are problematic from the ecological point of view and/or in some cases not readily accessible, which restricts their use.

Even though the process mentioned under 7) yields 3-substituted 2(3H)-benzothiazolones in very good yields, it has the disadvantage that, on the one hand, toxicologically unacceptable N-nitroso compounds are formed as intermediates and, on the other hand, the process is carried out in the presence of a solvent (xylene), which requires complicated and thus cost-intensive isolation of the product by concentration or evaporation of the solvent and drying of solvent-containing products. Moreover, 2(3H)-benzothiazolones which are unsubstituted in the 3-position are not accessible by this process.

EP Application 245 991 describes the preparation of benzothiazolones which are substituted on the nitrogen. Amongst a plurality of other possibilities, the route via 2-chlorobenzothiazole is also mentioned in this publication.

U.S. Pat. No. 4,353,919 describes the hydrolysis of benzothiazoles which are substituted by chlorine, bromine or alkoxy in the 2-position to give benzothiazolones, it being mentioned, in general, that the hydrolysis is carried out using an aqueous mineral acid at temperatures from 0° to 120° C. in the presence or absence of an inert solvent which is miscible with water.

From amongst the 12 examples, only 2 refer to the hydrolysis of 2-chlorobenzothiazoles. In each case, the reaction is carried out using highly concentrated hydrochloric acid and ethanol (1:1 mixture), giving 6-chloro-2(3H)-benzothiazolone in a yield of 83% starting from 2,6-dichlorobenzothiazole and 6-fluoro-2(3H)-benzothiazolone in a yield of 45% starting from 2-chloro-6-fluorobenzothiazole.

An example without an added solvent is not given.

It is known from the literature that 2-chlorobenzothiazole is stable in water up to 180° C. and hydrolyzes only at temperatures from 200° C., with partial decomposition (Chem. Ber. 13, 10), while the reaction in alcohol is markedly simpler. From Heterocyclic compounds, Volume 5, page 550, it is also known that the direct hydrolysis of 2-chlorobenzothiazoles is difficult and requires prolonged heating (25–45 hours) in alcoholic hydrochloric acid.

However, the disadvantage of using a solvent is that these added organic solvents, such as methanol, ethanol or glacial acetic acid, result in an increased pollution of the waste water with organic material.

There is therefore a demand for a process which avoids the abovementioned disadvantages and which can be realized in a simple fashion, starting from 2-aminobenzothiazoles, a multitude of which are readily accessible (preparation: EP 116 827). It should be possible to realize the process without substantial technical complications, producing the smallest possible amount of waste products for ecological reasons. Moreover, the desired valuable product should be made accessible not only in high yield, but also in high purity.

This object is achieved by a process for the preparation of 2(3H)-benzothiazolones (III) which are optionally substituted on the benzene ring. It comprises reacting a 2-aminobenzothiazole (I), which is optionally substituted on the benzene ring, with a diazotization agent in the presence of aqueous hydrochloric acid, if appropriate with addition of a chloride to give a diazonium chloride, reacting the diazonium chloride directly to give a 2-chlorobenzothiazole (II), which is optionally substituted on the benzene ring, and hydrolyzing the 2-chlorobenzothiazole, without intermediate isolation, at 120°–200° C. under reaction pressure.

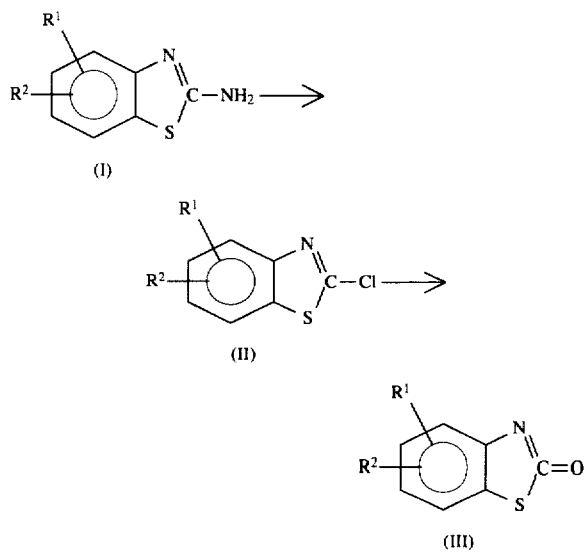

Substances which can be used as starting material are 2-aminobenzothiazoles of the formula (I) in which $R^1$ and $R^2$ are identical or different and are hydrogen, halogen, a cyano group or a nitro group.

The process for 2-aminobenzothiazoles of the formula (I) in which $R^1$ and $R^2$ are identical or different and represent hydrogen, fluorine, chlorine or a nitro group is preferred.

2-Aminobenzothiazoles of the formula (I) in which $R^1$ is hydrogen and $R^2$ is 4-fluoro, 4-chloro, 4-nitro, 6-fluoro, 6-chloro or 6-nitro, in particular 4-chloro, are also frequently used.

Diazotization of the 2-aminobenzothiazole is carried out using nitrosylsulfuric acid or nitrous acid, or salts of these, in particular alkali metal salts, preferably sodium nitrite, at a concentration of 100–300 mol %, in particular 100–250 mol %, based on 2-aminobenzothiazole employed, together with an aqueous acid, in particular hydrochloric acid.

The process is preferably carried out in the presence of 15–35%, in particular 20–30% hydrochloric acid, if appropriate with an added chloride, at temperatures from 0° to 50° C.

Chlorides which can be employed are alkali metal chlorides or alkaline earth metal chlorides, in particular alkaline earth metal chlorides, preferably $CaCl_2$.

After the reaction has ended, the excess nitrite (diazotization agent) is conventionally removed by adding urea or amidosulfonic acid, preferably in the form of aqueous solutions, or other reagents which are suitable for destroying excess nitrite (diazotization agent).

The resulting reaction mixture is subsequently hydrolyzed in a sealed pressure vessel at temperatures from 120° to 200° C. without further addition of a solvent, in particular an organic solvent. In many cases, it has shown to be expedient to carry out the process at temperatures from 130° to 180° C., in particular 130° to 150° C., preferably 135° to 150° C. The reaction time required depends, on the one hand, on the batch size and, on the other hand, also on the temperatures in question. In general, a reaction time of 1 to 10, in particular 3 to 5, hours is shown to be sufficient. The reaction is carried out under pressure, in particular under the reaction pressure which is established in each case. The pressure is conventionally 1.5 to 20, in particular 2 to 16, bar.

After the mixture has cooled to 20° C., the finely-crystalline product is isolated and dried in the customary manner.

This gives 2(3H)-benzothiazolones in a yield of 82–94%, which corresponds to a yield of 90 to 97% per reaction step.

The resulting yields over 2 steps (starting from 2-aminobenzothiazoles) are substantially higher than as described in U.S. Pat. No. 4,353,919 for the 1 step reaction (starting from the 2-chlorobenzothiazoles). 6-Fluoro-2 (3H)-benzothiazolone is obtained in a yield of 85% in the process according to the invention (in contrast to 45% in U.S. Pat. No. 4,353,919), and 6-chloro-2(3H)-benzothiazolone in a yield of 91.6% (in contrast to 83% in U.S. Pat. No. 4,353, 919).

The process according to the invention is particularly suitable for industrial use in as far as, on the one hand, it dispenses with yield-reducing and costly intermediate isolation of 2-chlorobenzothiazoles and, on the other hand, it only requires relatively short reaction times. Moreover, it is an environmentally friendly process since it makes do entirely without solvents which pollute the waste water and, moreover, yields 2(3H)-benzothiazolones in very high yield and good quality.

If desired, the process can also be applied to the isolated 2-chlorobenzothiazoles of the formula (II), by hydrolyzing the latter in mineral acids without addition of solvents under reaction pressure at 120° to 200° C., in particular 130° to 180° C., preferably 130° to 150° C.

To this end, it is possible to employ chlorobenzothiazoles of the formula (II) in which $R^1$ and $R^2$ are identical or different and are hydrogen, halogen, cyano or the nitro group.

The examples which follow are intended to illustrate the process according to the invention without limiting it thereto.

EXAMPLE 1

768 g of 30% hydrochloric acid are introduced into a 2 l pressure vessel, and 195.4 g of moist 2-amino-4-chlorobenzothiazole with a dry matter content of 50.92% are introduced at room temperature. After 71.3 g of calcium chloride have been added, the mixture is heated for 30 minutes at 50° C. and then again cooled to 20° C. Then, 174.4 g of aqueous 40% sodium nitrite solution are uniformly metered in below the surface at 20°–24° C. in the course of 8 hours while stirring thoroughly. After metering in has ended, stirring is continued for 2 hours at 20°–24° C. Then, excess nitrite is destroyed by slowly adding approximately 40 g of aqueous 18% urea solution. The reaction vessel is subsequently sealed and the reaction mixture is heated for 3 to 5 hours at 130°–135° C. (pressure 4–5 bar), with vigorous stirring. After the reaction mixture has cooled to 20° C., the finely-crystalline product is filtered off with suction, washed until neutral and dried at 60° C. to constant weight.

96.8 g of 4-chlorobenzothiazol-2-one containing 97% of pure substance (corresponding to 93.9% yield) are obtained. Product which is undissolved under alkaline conditions has a DSC melting point of 203°–203.5° C.

EXAMPLE 2

384 g of 30% hydrochloric acid are introduced into a 1,000 ml pressure vessel, and 50.3 g moist 2-amino-6-chlorobenzothiazole (pure substance content: 99.2%) are added at room temperature. After 35.7 g of calcium chloride have been added, the mixture is heated for 30 minutes at 50° C. and again cooled to 20° C. Then, 87.2 g of aqueous 40% sodium nitrite solution are uniformly metered in below the surface at 20°–24° C. in the course of 5 hours, while stirring vigorously. After metering in has ended, stirring is continued for 1 hour at 20°–24° C. Then, excess nitrite is destroyed by slowly adding approximately 20 g of aqueous 18% urea solution. The reaction vessel is subsequently sealed and the reaction mixture is heated for 4 hours at 145°–150° C. (pressure 5–6 bar), with vigorous stirring. After the reaction mixture has cooled to 20° C., the beige product is filtered off with suction, washed until neutral and dried at 60° C. to constant weight with a 46.4 g of 6-chlorobenzothiazol-2-one of pure substance content of 99% (corresponding to 91.6% yield) are obtained. The product which has been precipitated under alkaline conditions has a DSC melting point of 211.2° C.

EXAMPLE 3

28.75 g of 2-amino-6-nitrobenzothiazole, 210 g of 30% hydrochloric acid and 29.5 g of water are introduced into a 750 ml pressure vessel at room temperature and subsequently heated to 50° C. After the reaction mixture has been stirred for 30 minutes, it is cooled to 20° C. 50.75 g of aqueous sodium nitrite solution are then metered in at a uniform rate in the course of 3 hours at 20°–30° C., with very vigorous stirring. After metering in has ended, stirring is continued for 2.5 hours at 20°–30° C. Then, excess nitrite is removed by adding approximately 15 g of 18% aqueous urea solution. The reaction vessel is subsequently sealed, and the reaction mixture is heated for 5 hours at 140°–150° C. (pressure approximately 4 bar). After the mixture has cooled to 20° C., the crystalline product is filtered off with suction, washed until neutral and dried at 60° C. to constant weight. 27.3 g of 6-nitrobenzothiazol-2-one with a pure substance content of 97.8% are obtained (corresponding to 92.4% yield). The product which is redissolved under alkaline conditions has a DSC melting point of 252.5° C.

EXAMPLE 4

33 g of 2-amino-4,5-dichlorobenzothiazole, 241 g of 30% hydrochloric acid and 33.9 g of water are introduced into a 750 ml pressure vessel at room temperature and subsequently heated to 50° C. After the mixture has been stirred for 30 minutes, 58.3 g of aqueous, 40% sodium nitrite solution are metered in at a uniform rate in the course of 3 hours at 50° C., with vigorous stirring. After metering in has ended, stirring is continued for 4 hours at 50° C. Excess nitrite is then removed by adding approximately 15 g of 18% aqueous urea solution. The reaction vessel is subsequently sealed, and the reaction mixture is heated for 4 hours at 140°–150° C. (pressure approximately 6 bar). After the mixture has cooled to 20° C., the crystalline product is filtered off with suction, washed with water and dried at 60° C. to constant weight. 27.9 g of 4,5-dichlorobenzothiazol-2-one with a pure substance content of 97.2% are obtained (corresponding to 81.8% yield) with a DSC melting point of 229.1° C.

EXAMPLE 5

22.4 g of 2-amino-6-fluorobenzothiazole (pure substance content: 97%) and 191.1 g of 30% hydrochloric acid are introduced into a 750 ml pressure vessel at room temperature. The mixture is subsequently heated for 30 minutes at 50° C. and then cooled to 10° C. Then, 46.7 g of aqueous, 40% sodium nitrite solution are metered in at a uniform rate in the course of 1 hour at 10° C., with vigorous stirring. After metering in has ended, stirring of the reaction mixture is continued for 12 hours at 20° C. Excess nitrite is then removed by adding approximately 12.5 g of 18% aqueous urea solution. The reaction vessel is subsequently sealed, and the reaction mixture is heated for 5 hours at 140°–150° C. (pressure approximately 4–5 bar). After the mixture has cooled to 20° C., the gray, crystalline product is filtered off with suction, washed with a small amount of water and dried at 60° C. to constant weight. 18.9 g of 6-fluorobenzothiazol-2-one with a pure substance content of 97.7% are obtained (corresponding to 85% yield). The product which is redissolved under alkaline conditions has a melting point of 188.4° C.

We claim:

1. A process for the preparation of 2(3H-benzothiazolones which comprises the steps of reacting a 2-amino-benzothiazole with a diazotization agent in the presence of hydrochloric acid to give a diazonium chloride, reacting the diazonium chloride without intermediate isolation to form a 2-chlorobenzothiazole, and hydrolyzing the 2-chlorobenzothiazole, without intermediate isolation, at 120°–120° C. under reaction pressure, wherein the complete reaction is conducted without the addition of organic solvents.

2. The process as claimed in claim 1, wherein a 2-aminobenzothiazole of the formula I

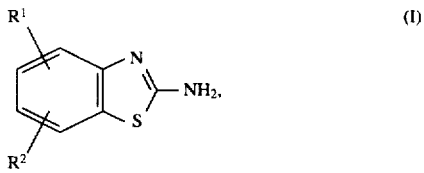

(I)

in which $R^1$ and $R^2$ are identical or different and are hydrogen, halogen, the cyano group or the nitro group, is employed.

3. The process as claimed in claim 2, wherein a 2-aminobenzothiazole of the formula (I), in which $R^1$ and $R^2$ are identical or different and are hydrogen, fluorine, chlorine or a nitro group, is employed.

4. The process as claimed in claim 2, wherein a 2-aminobenzothiazole of the formula (I), in which $R^1$ is hydrogen and $R^2$ is fluorine, chlorine or a nitro group, is employed.

5. The process as claimed in claim 2, wherein a 2-aminobenzothiazole of the formula (I) in which $R^1$ is hydrogen and $R^2$ is 4-fluoro, 4-chloro or 4-$NO_2$, is employed.

6. The process as claimed in claim 2, wherein a 2-aminobenzothiazole of the formula (I) in which $R^1$ is hydrogen and $R^2$ is 6-fluoro, 6-chloro or 6-$NO_2$, is employed.

7. The process as claimed in claim 1, wherein a 2-amino-4-chlorobenzothiazole is employed.

8. The process as claimed in claim 1, wherein the hydrochloric acid is employed at a concentration of 15 to 35% by weight.

9. The process as claimed in claim 1, wherein the chloride employed is an alkali metal chloride or alkaline earth metal chloride.

10. The process as claimed in claim 1, wherein the diazotization agent is nitrosylsulfuric acid or nitrous acid or salts thereof.

11. The process as claimed in claim 1, wherein hydrolysis is carried out at temperatures of 130°–180° C.

12. A process for the preparation of 2(3H)-benzothiazolones which are optionally substituted on the benzene ring, which comprises the step of hydrolyzing a 2-chlorobenzothiazole which is optionally substituted on the benzene ring, in a mineral acid selected from the group consisting of hydrochloric acid, sulfuric acid and phosphoric acid, without the addition of a solvent, under reaction pressure at 120°–200° C.

13. The process as claimed in claim 12, wherein 2-chlorobenzothiazole of the formula III

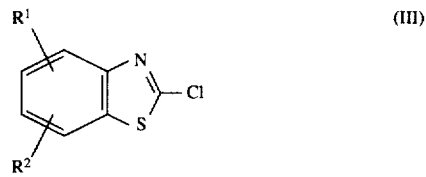

(III)

in which $R^1$ and $R^2$ are identical or different and are hydrogen, halogen, cyano or the nitro group is employed.

14. The process as claimed in claim 8, wherein the hydrochloric acid is employed at a concentration of 20 to 30% by weight.

15. The process as claimed in claim 9, wherein the chloride employed is a alkaline earth metal chloride.

16. The process as claimed in claim 9, wherein the chloride employed is $CaCl_2$.

17. The process as claimed in claim 10, wherein the diazotization agent is an alkali metal salt.

18. The process as claimed in claim 10, wherein the diazotization agent is sodium nitrite.

19. The process as claimed in claim 11, wherein hydrolysis is carried out at temperatures of 130°–150° C.

20. The process as claimed in claim 11, wherein hydrolysis is carried out at temperatures of 135°–150° C.

21. The process as claimed in claim 12, wherein the two-chlorobenzothiazole is hydrolyzed at a temperature of 130°–180° C.

22. The process as claimed in claim 12, wherein the two-chlorobenzothiazole is hydrolyzed at a temperature of 135°–150° C.

23. A process as claimed in claim 1, wherein the 2-aminobenzothiazole is substituted on the benzene ring.

24. A process as claimed in claim 1, wherein the step of reacting a 2-amino-benzothiazole with a diazotization agent in the presence of hydrochloric acid includes the addition of a chloride.

* * * * *

UNITED STATES PATENT AND TRADEMARK OFFICE
CERTIFICATE OF CORRECTION

PATENT NO. : 5,594,145
DATED : January 14, 1997
INVENTOR(S) : Klaus Forstinger, et al It is certified that error appears in the above-indentified patent and that said Letters Patent is hereby corrected as shown below:

In claim 21, at column 6, line 55, "two-chlorobenzothiazole" should read --2-chlorobenzothiazole--.

In claim 22, at column 6, line 58, "two-chlorobenzothiazole" should read --2-chlorobenzothiazole--.

Signed and Sealed this

Twenty-second Day of July, 1997

Attest:

BRUCE LEHMAN

Attesting Officer

Commissioner of Patents and Trademarks